United States Patent [19]

Thompson et al.

[11] Patent Number: 5,061,857

[45] Date of Patent: Oct. 29, 1991

[54] WAVEGUIDE-BINDING SENSOR FOR USE WITH ASSAYS

[75] Inventors: Richard B. Thompson, Baltimore, Md.; Carl A. Villarruel, Burke, Va.

[73] Assignee: The United States of America as represented by the Secretary of the Navy, Washington, D.C.

[21] Appl. No.: 610,895

[22] Filed: Nov. 9, 1990

[51] Int. Cl.$^5$ ............................................. G01N 21/64
[52] U.S. Cl. ............................... 250/458.1; 250/461.2; 136/527; 385/30; 385/12
[58] Field of Search ............... 250/458.1, 461.1, 461.2; 350/96.33, 96.30, 96.15; 486/527, 805, 807

[56] References Cited

U.S. PATENT DOCUMENTS

| | | | |
|---|---|---|---|
| 4,447,546 | 5/1984 | Hirschfield | 250/227.11 |
| 4,558,014 | 12/1985 | Hirschfeld et al. | 436/527 |
| 4,654,532 | 3/1987 | Hirschfield | 250/461.2 |
| 4,671,938 | 6/1987 | Cook | 436/527 |
| 4,678,267 | 7/1987 | Burns et al. | 350/96.15 |
| 4,716,121 | 12/1987 | Block et al. | 436/527 |
| 4,834,496 | 5/1989 | Blyler, Jr. et al. | 350/96.33 |
| 4,844,868 | 7/1989 | Glass | 436/805 |
| 4,880,752 | 11/1989 | Keck et al. | 436/528 |
| 4,909,990 | 3/1990 | Block et al. | 436/827 |
| 4,981,338 | 1/1991 | Bobb et al. | 350/96.24 |

OTHER PUBLICATIONS

"Sensitivity Enhancement for Evanescent Wave-Excited Fiber Optic Fluorescence Sensors", Thompson et al., SPIE, vol. 1204, pp. 35-41.

*Primary Examiner*—Carolyn E. Fields
*Assistant Examiner*—Drew A. Dunn
*Attorney, Agent, or Firm*—Thomas E. McDonnell; Barry A. Edelberg

[57] ABSTRACT

An optical waveguide-binding sensor which increases sensor sensitivity to fluorescence detection during assays of liquids based on adjustments in the V number along the optical waveguide. The sensing waveguide includes a mode converting section where the V number of the wavguide gradually increases from the distal sensing end of the mode converting section to the proximal end of the mode converting section. The gradually change in V number can be accomplished by either gradually inwardly tapering waveguide along the sensor portion from the proximal end, or by gradually varying the dopant concentration along the sensing portion. The sensor tapers in diameter to change the V number along the distal end of the optical waveguide. The present invention increases the efficiency of fluorescence detection by converting weakly-guided high-order modes of fluorescence radiation at the distal end into lower-order modes at the proximal and increases the efficiency of fluorescent excitation by converting low order mode entering the proximal end into weakly-guided high order modes at the sensing end. At the sensing end, these weakly guided modes cn strengthen the evanescent excitation wave.

16 Claims, 2 Drawing Sheets

WAVEGUIDE-BINDING SENSOR FOR USE WITH ASSAYS

BACKGROUND OF THE INVENTION

1. Field of the Invention

The present invention relates generally to waveguide-binding sensors for use in fluorescence assays, and, more particularly, to methods for increasing the sensitivity of a fiber-optic waveguide-binding sensor which remotely senses fluorescence radiation during assays of liquid solutions.

2. Background of the Invention

The evanescent wave portion of an electromagnetic field produced by light propagating through an optical waveguide characteristically penetrates a few hundred nanometers into the medium surrounding the optical waveguide. This evanescent wave can excite fluorescent molecules, e.g., fluorophores, to fluoresce when binding pairs of molecules are near the optical waveguide surface. The application of this phenomenon to an immunoassay sensor, wherein the biological recognition (binding) of an antigen by antibodies attached to the waveguide surface with concomitant displacement of fluorescent-labeled antigen is measured as a change in fluorescence, was first disclosed in "A New Immunoassay Based on Fluorescence Excitation by Internal Reflection Spectroscopy" by Kronick and Little, *Journal of Immunological Methods*, 1975, Vol. 8, page 235.

The use of optical fibers as a special class of waveguides for immunoassay sensors is also known. For example, U.S. Pat. No. 4,447,546 discloses the use of optical fibers as waveguides which capture and conduct fluorescence radiation emitted by molecules near their surfaces. However, conventional waveguide-binding sensors for use with assays of aqueous fluids have demonstrated inadequate sensitivity. Specifically, poor sensor performance is attributed at least in part to the small size of the sample being analyzed, typically one or several monolayers in depth, and the small surface area of the optical waveguide, which factors limit the number of fluorophores which may be excited. More serious sensor performance degradation is mainly attributable to the effects of a weak evanescent wave, which fails to excite the fluorophores enough to produce detectable levels of fluorescence.

Increasing the strength of the evanescent wave penetrating into a fluid sample to be assayed increases the amount of fluorescence, thereby increasing sensor sensitivity. However, the evanescent wave propagates as higher-order modes within and near the outer surface of an optical waveguide core. These higher-order modes are weakly-guided, lossy, and can easily leak at a discontinuity or a bending point along the waveguide.

The use of tapered optical fibers to increase the sensitivity of fiber-optic assay systems is known. For example, U.S. Pat. Nos. 4,654,532 and 4,909,990 disclose the use of tapered fibers to increase the numerical aperture of the proximal end of the sensor, i.e., the sensing portion located at the near end of the fiber, as a means of increasing sensor sensitivity. In the disclosed systems, an unclad tapered optical fiber which is completely isolated from the sample fluid is mounted on the proximal end of a sensing fiber. The tapered portion forces the convergence of input excitation radiation prior to entry into the sensing portion of the fiber, thus increasing the numerical aperture from the proximal to distal end and, allegedly, increasing sensor sensitivity.

The present inventors recognize, however, that the introduction of a tapered section of the optical waveguide at the proximal end fails to address certain important issues central to the sensitivity of these sensors, especially in remote sensing applications. In particular, the higher order modes propagating in the section of the waveguide where the fluorophores are found (the distal end) comprise the evanescent wave and the bulk of the fluorescence coupled back into the fiber. These higher order modes typically propagate with greater loss than lower order modes.

The sensitivity of known fiber-optic sensors is further reduced by loss of poorly-guided fluorescence radiation propagating along the length of an optical fiber. Like the evanescent wave, fluorescence radiation from sources on the fiber core surface propagates in the higher-order modes and is equally susceptible to losses due to microbending of the optical fiber.

Known fiber-optic sensors suffer from the additional disadvantage that their performance is dependent on the length of the waveguide.

SUMMARY OF THE INVENTION

It is accordingly a principal object of the present invention to provide a waveguide-binding sensor having improved sensitivity for use with fluorescence assays.

It is another object of the present invention to provide a tapered type of optical waveguide-binding sensor with improved transmission of the excitation radiation and resulting fluorescence radiation within the sensor.

It is a further object of the present invention to provide an improved waveguide-binding sensor suitable for remote sensing in which the strength of the sensor signal is less dependent on the length of the waveguide.

These and other objects are achieved in accordance with the present invention by a sensing waveguide having a mode converting section with a distal end having a normalized frequency parameter (V-number) less than or equal to the V number of the rest of the waveguide including the proximal end of the mode converting section. For example, the distal end of an optical waveguide for use as the sensing element of a waveguide-binding sensor can be inwardly tapered. In accordance with a further aspect of that embodiment of the present invention, the core diameter is so tapered at or immediately adjacent the sensing portion of the optical waveguide. Throughout the present specification and claims, all references to tapering of the waveguide mean tapering of the light-carrying section of the waveguide, i.e., no reference is made to tapering of any covering or coating which might surround the waveguide, which covering may or may not be tapered. Usually, the mode converting section of the waveguide will be unclad.

In another embodiment of the present invention, the V number of the waveguide can be made lower at the distal end by a employing a gradual change in the refractive index of the waveguide and/or surrounding medium at or near the distal end of the waveguide so that at the sensing portion, the difference between the refractive index of the light-carrying section of the waveguide (as opposed to a protective coating or cladding) and the refractive index of the fluid sample is significantly smaller than the difference between the refractive index of the light-carrying section of the waveguide at the proximal end section of the waveguide and its surrounding medium (for example, a cladding or coating or simply the surrounding environment). The change in refractive index can be accomplished, for example, by gradually changing the concentration of a dopant in the waveguide and/or its surrounding medium at or immediately adjacent the sensing end of the waveguide. Again, the mode converting section of the waveguide will usually be unclad.

According to the present invention, the lower-order modes of excitation radiation are thus strongly converted into higher-order modes. This conversion effectively strengthens the evanescent wave, extending the useful area of the distal end of the waveguide by promoting a successive conversion of low order to high order modes in the direction of light source to sample and, in the direction from sample to detector, the conversion of weakly guided higher-order modes of fluorescence radiation into lower-order modes. Lower-order modes are much less susceptible to bending losses when propagating through the waveguide.

These and other objects, features and advantages of the invention are disclosed in or apparent from the following detailed description of preferred embodiments.

BRIEF DESCRIPTION OF THE DRAWINGS

The preferred embodiments are described with reference to the drawings in which.

DESCRIPTION OF THE PREFERRED EMBODIMENTS

Figure 1:
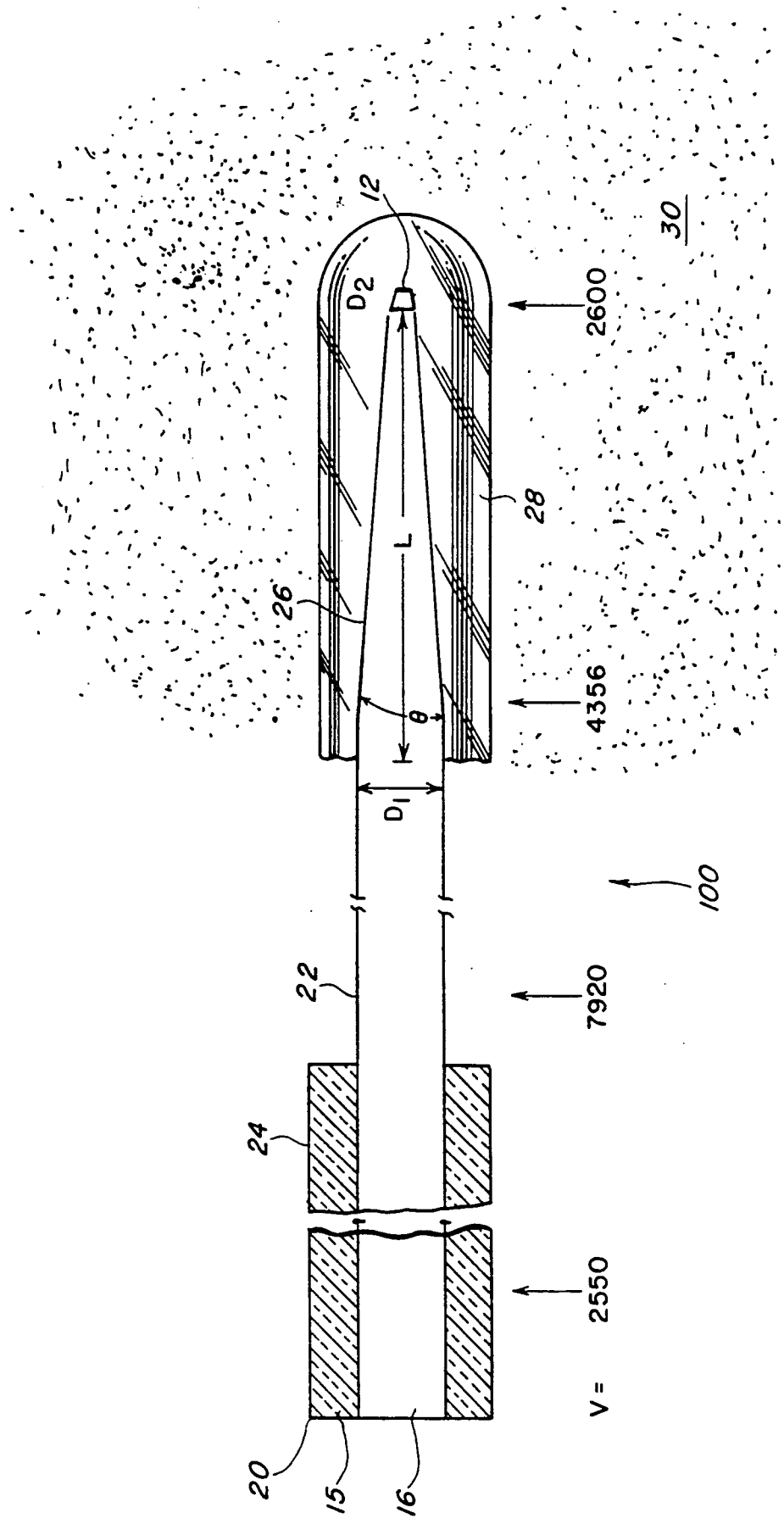
FIG. 1 is a diagrammatic side elevation view of a waveguide-binding sensor in accordance with the present invention.

Referring to FIG. 1, a fiber-optic waveguide-binding sensor 100 according to the present invention comprises an elongated optical fiber 20 having a proximal end section 24, a midsection 22 and a distal end section 26, each of which is adapted to propagate along its length optical excitation radiation through multiple total internal reflections. Preferably, optical fiber 20 has a substantially circular cross-section, but other fiber geometries, such as slab-type optical waveguides, can be used. Optical fiber 20 is advantageously a multi-mode fiber, and is constructed from any one of a large number of substantially homogeneous materials which are optically transparent to excitation radiation, e.g., glass, quartz and synthetic polymers such as polymethylmethacrylates, fluoropolymers and the like. Each section of optical fiber 20 has an index of refraction greater than the refractive index of the fluid sample being assayed, e.g., $n = 1.33$ for an aqueous fluid sample.

Preferably, proximal end section 24, midsection 22 and distal end section 26 are different from each other in both structure and normalized frequency parameter (V number), as discussed in greater detail below. Proximal end section 24 is a conventional cladded optical fiber of arbitrary length which comprises a cladding 15 with an index of refraction $n_1$, and a fused silica fiber core 16 with an index of refraction $n_2$. Midsection 22 consists of optical fiber core 16 with cladding 15 removed so that core 16 is directly exposed to the environment. Midsection 22 can be exposed to any medium whose refractive index is less than that of core 16. Distal end section 26 is formed by tapering core 16 from an initial diameter $D_1$ to a terminal diameter $D_2$ at tip 12 over a length L, and is coated with a layer 28 of reagent which contains a predetermined concentration of a selected tagging component. Reagent 28 advantageously is a coating one or several monolayers thick, i.e., typically a few hundred nanometers. The tagging component is selected to attract and bind to an analyte, the presence of which within fluid sample 30 is to be detected, to form binding pairs which emit fluorescence radiation when subjected to high energy radiation from an evanescent wave. Reagent 28 advantageously is of the type disclosed in U.S. Pat. No. 4,447,546, the entirety of which is incorporated herein by reference. Reagent layer 28 is shown greatly enlarged in FIG. 1 for the sake of clarity.

Figure 2:
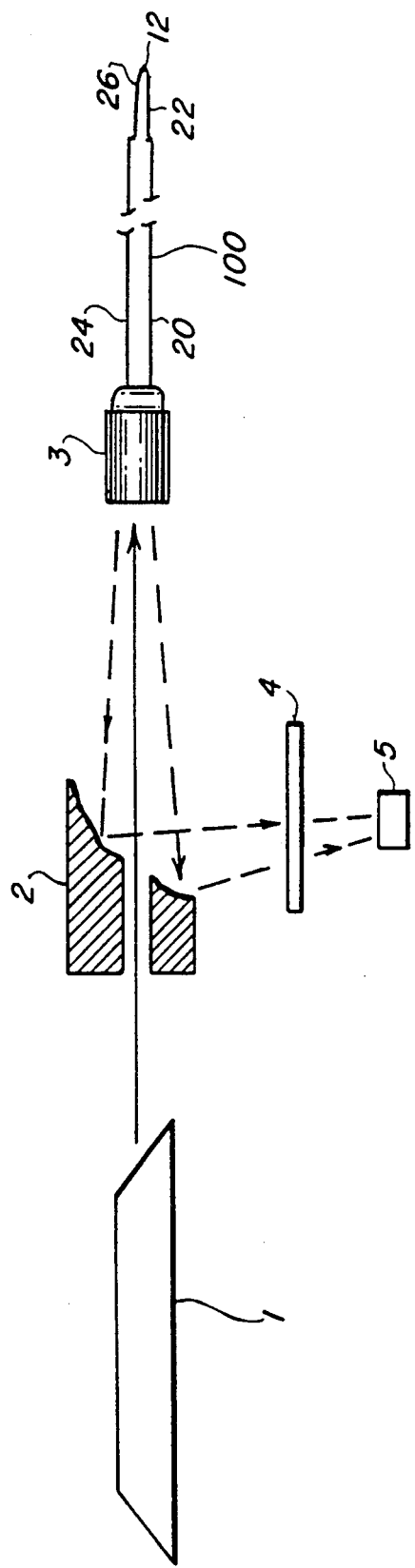
FIG. 2 is a schematic block diagram of an assay measuring system incorporating a waveguide-binding sensor according to the present invention.

Referring to FIG. 2, a fluorimeter 200 incorporating fiber-optic waveguide-binding sensor 100 comprises a light source such as a laser source 1, beam-splitting mirror 2, objective 3, optical filter 4 and photodetector 5. Laser source 1 provides optical radiation of a predetermined wavelength, chosen on the basis of the tagging component selected for the assay of interest, to excite binding pairs formed within reagent 28 when distal end section 26 contacts a fluid sample, and cause these binding pair to emit fluorescent radiation. Preferably, laser 1 provides this radiation over only a narrow wavelength band specifically chosen to maximize the excitation of, and consequent emission of fluorescent radiation from, the binding pairs. The optical beam emitted from laser 1 passes through beam-splitting mirror 2 and illuminates objective 3 which, in turn, focuses the light beam into proximal end section 24 of optical fiber 20. In an exemplary embodiment which has proved satisfactory in testing, a Liconix 4214NB HeCd laser emitting 10 mw of power at a wavelength of 442 nm constitutes laser 1, a Nikon PH2 PLAN 20×0.40 NA ELWD objective constitutes objective 3, and a General Fiber Optics or Quartz et Silice plastic clad fused silica fiber having a 600 μm core and 0.36 NA constitutes optical fiber 20.

The optical beam travels through proximal end section 24 and midsection 22 until reaching distal end section 26. Distal end section 26 emanates evanescent wave-induced excitation radiation into its reagent 28, which excites fluorescence radiation from binding pairs therein. Fluorescence radiation near the surface of fiber core 16 forming distal end section 26 is captured and converted from high-order modes into low-order modes by reason of the tapered configuration of distal end section 26, and coupled back into the rest of optical fiber 20.

Objective 3 focuses fluorescence radiation travelling back through optical fiber 20 onto beam-splitting mirror 2, where the radiation is reflected through optical filter 4 and projected onto photodetector 5. A PIN photodiode advantageously constitutes photodetector 5. Photodetector 5 converts the fluorescence radiation into an electrical signal which is processed in a conventional manner to verify the presence of a tagged component within the fluid sample.

The angle of the taper with the optical axis of the fiber must not exceed the critical angle for the fiber to avoid significant transmission loss. As an example, $D_1$, $D_2$, and L preferably are 600 microns, 200 microns and 2 cm, respectively. However, it will be appreciated that these dimensions advantageously are varied in dependence on sensitivity requirements that are specific to each assay performed.

The degree of taper at distal end section 26 advantageously is determined according to the effective numerical aperture at tip 12 of optical fiber 20. If the angle of the taper $\theta$ defined by the converging wall of distal end section 26 exceeds the numerical aperture of tip 12, leakage occurs through the tapered wall. In order to minimize loss, the diameter at distal end section 26 thus preferably very gradually decreases to produce an essentially lossless taper. In the illustrative example given above, taper angle $\theta$ preferably does not exceed 2°. However, it has been experimentally observed that, within the aforementioned restrictions, the taper geometry is not critical to sensor performance, and that a nonlinear taper (for example, convex, concave, or complex curvature) may be used for the taper geometry, provided that the angle of taper never exceeds the critical angle. The taper may also be stepwise, provided that the steps are extremely small in comparison to the wavelength, e.g., $\Delta NA/\lambda$ is less than or equal to about 0.001. A stepwise taper meeting that definition is essentially continuous and the term "continuous taper" as used in the present specification and claims is defined as including such a stepwise taper.

The desired taper geometry of optical fiber 20 may be achieved in any conventional manner. For example, one practical method involves the timed immersion of an optical fiber in and withdrawal from a corrosive etching solution, such as hydrofluoric acid (HF). Immersing distal end section 26 for a short period of time and withdrawing it at a predetermined rate produces a fiber core with a gradual and continuous taper, as shown in FIG. 1. Another conventional method, as disclosed, for example, in U.S. Pat. No. 4,607,912, is to thermally taper an optical fiber by heating and then stretching an unjacketed fiber.

The penetration depth of the evanescent wave into reagent 28 is a function of the wavelength of the evanescent wave and the refractive indices of the waveguide and its surroundings. The wavelength band of the optical radiation transmitted through optical fiber 20 typically ranges between 200-1200 microns, however the specific operating frequency chosen during sensor operation is dependent upon the type of tagging component being used in the assay. The wavelength which maximizes the fluorescence radiation emitted from the binding pairs determines the operating wavelength of the sensor.

Sensor sensitivity, i.e., the ability of the sensor to detect fluorescence radiation, is based in part on the propagating characteristics of the optical waveguide. More specifically, sensor sensitivity is strongly influenced by two critical factors: 1) the power of the evanescent wave creating the excitation radiation; and 2) the efficiency with which fluorescence radiation excited by the evanescent wave is coupled back through the length of the optical waveguide. Applicants have recognized that both of these critical factors are in turn strongly influenced by V number. Because the V number is directly proportional to the waveguide core diameter, tapering the diameter of distal end section 26 maximizes both of these critical factors and, hence, increases sensor sensitivity. The effects of tapering distal end section 26 on sensor sensitivity will be described in more detail hereinbelow with reference to an exemplary embodiment.

FIG. 1 shows the V number for each section of an optical fiber 20 having the dimensions described above. Proximal end section 24 and midsection 22 each have a fixed core diameter and, therefore, a fixed V number. Proximal end section 24 has a V number of 2550, and midsection 22 has a V number of 7920 when the surrounding medium is air. The tapering core diameter of distal end section 26 varies the V number from 2600 at tip 12 to 4356 at a location just before the beginning of midsection 22. By reducing the core size of distal end section 26, lower-order modes of excitation radiation are converted into higher-order modes which penetrate directly into the fluid sample being assayed, thus effectively strengthening the evanescent wave and extending the useful area of the distal end of the waveguide by promoting a successive conversion of low order to high order modes in the direction of light source to sample and, in the direction from sample to detector, the conversion of weakly guided higher-order modes of fluorescence radiation into lower-order modes.

Fluorescence radiation launched into the waveguide from the surface propagates predominantly as weakly-guided, higher-order modes which are easily stripped by abrupt changes in V number. By tapering distal end section 26, these higher-order modes of the florescence radiation propagating in the reverse direction along distal end section 26 of optical fiber 20 toward proximal end section 24 are converted into lower-order modes as the fiber core widens. These lower-order modes are much less likely to be stripped when coupled back to proximal end section 24. Because $V = 2\pi a/\lambda \times (n_1^2 - n_2^2)^{1/2}$ (Eq. 1), where a is the radius of the fiber and $n_1$ and $n_2$ are the indices of refraction of the fiber core and the medium surrounding the fiber core, respectively, the effect of varying the index of refraction is to concomitantly vary the V number of an optical fiber. Generally, the effect of cladding 15 on the proximal end section 24 will be to decrease $n_2 - n_1$ on that section and thus produce a V number which is substantially lower that the V number at unclad midsection 22. The losses caused by the drop in V number between the clad and unclad sections of optical fiber 20 are advantageously further compensated for by converting the modes of fluorescence radiation well in advance of the discontinuity. Thus, the degree of tapering is chosen so that the distal end of the fiber immersed in solution has a lower V number than the clad, proximal end. For example, an optical fiber 20 is selected having refractive indices of $n = 1.41$ for cladding 15 and $n = 1.45$ for fiber core 16. (The effect of the refractive index of reagent 28 on the V number is probably negligible because of the very small coating thickness.) Note that Eq. 1, and thus the present invention, can be applied by analogy to other optical waveguide geometries, such as slab waveguides.

Eq. 1 suggests an additional method of accomplishing the present invention. Mode conversion can be accomplished by gradual (zero or essentially zero loss) variation of the refractive index of the waveguide and/or its surrounding medium at or adjacent to the distal end portion. Variation of the refractive index of the waveguide can be accomplished, for example, by varying the concentration of dopant gradually along that portion of the light-carrying section of the waveguide or along that portion of the cladding section of the waveguide. One way, but not the only way, of gradually varying the concentration of dopant along a length of waveguide is to dope the length of waveguide and then dip the doped length of waveguide into a leaching solution, varying the rate at which the waveguide is removed from the leaching solution to produce a continuous variation in dopant concentration along that length of waveguide. Additionally, mode conversion can be accomplished by a combination of varying the refractive index of the waveguide and/or its surrounding medium with tapering.

Sensor 100 is particularly suited for use in a variety of assay applications. For example, sensor 100 can be mounted on the tip of a catheter and inserted into a blood vessel to provide continuous, real-time, remote detection of a chemical analyte, e.g., toxins, hormones, illegal drugs, etc., present therein. Reagent 28 is treated to include a high concentration of complementary antibodies which attract and bind with the antigens targeted for detection.

As another example, sensor 100 forms an environmental sensor which detects the presence of environmental gases through fluorescence quenching. In this application, a sensor 100 having a predetermined concentration of a tagging component for binding with a desired gas to be monitored, e.g., oxygen, nitrogen, etc., is introduced into the environment to be monitored. Binding pairs within reagent 28 continuously emit a constant level of fluorescence radiation into distal end section 26 under quiescent conditions. Changes in the concentration of the detected gas caused by some external factor, i.e., fire or smoke, produces a proportional change in the amount of fluorescence radiation being collected and coupled back into proximal end section 24 of optical waveguide 20. This change in the level of fluorescence radiation emitted by the binding pairs within reagent 28, known as fluorescence quenching, is measured by detector 5.

In still other exemplary applications, reagent 28 of sensor 100 is selected to form a sensing device for detecting the presence of oil in the ground, ground water, or the ocean.

The degree of mode conversion which the present invention must achieve to significantly enhance the sensitivity of a fiber optic sensor depends on the application for which the sensor is being used. In some measurements, a small degree of mode conversion will provide usefully enhanced sensitivity, while other measurements may require higher sensitivity and consequently a larger degree of mode conversion. Usually, the mode converting section should convert at least one percent of the low order modes transmitted into its proximal end into high order modes at its distal end. Generally, this degree of mode conversion is assured if the ratio of the V number at the distal end of the mode converting section to the V number at the proximal end of mode converting section is greater than about 2 or 3. It should be emphasized, however, that the above parameters for V number ratio and mode conversion are guidelines and not absolute limits.

Other modifications and variations to the invention will be apparent to those skilled in the art from the foregoing disclosure. Thus, while only certain embodiments of the invention have been specifically described herein, it will be apparent that numerous modifications may be made thereto without departing from the spirit and scope of the invention.

What is claimed is:

1. A mode converting multimode sensing waveguide for use in fluorescence assays, comprising:

a distal end section including a mode converting section having a proximal end and a distal end and a V number which is higher at said proximal end than at said distal end, said V number changing from said proximal end to said distal end at a rate sufficiently gradual that essentially no transmission loss occurs through said mode converting section, the difference in V numbers between said proximal end and said distal end being sufficient to convert a significant number of low order modes of an excitation wave transmitted from said proximal end of said distal end section to high order mode at said distal end of said distal end section, said distal end of said distal end section corresponding to a distal end of said waveguide and being coated with a tagging component for forming a fluorescent binding pair with an analyte;

a proximal end section of essentially constant V number extending from said proximal end of said distal end section to a proximal end of said waveguide.

2. The waveguide of claim 1, wherein said mode converting section is inwardly tapered from its proximal end and said proximal end of said waveguide has an essentially constant diameter.

3. The waveguide of claim 2, wherein the ratio of the V number at the distal end of said mode converting section to the V number at the proximal end of said mode converting section is greater than about 2.

4. The waveguide of claim 3, wherein the ratio of the V number at the distal end of said mode converting section to the V number at the proximal end of said mode converting section is greater than about 3.

5. The waveguide of claim 1, wherein said waveguide is a fiber.

6. The waveguide of claim 1, wherein said proximal end section has a cladding and the portion of said waveguide from the mode converting section to the distal end of said waveguide is unclad.

7. The waveguide of claim 1, wherein said mode converting section has a dopant concentration which gradually changes from the distal end of said mode converting section to the proximal end of said mode converting section so as to gradually increase the refractive index of said waveguide from the distal end of said mode converting section to the proximal end of said mode converting section.

8. The waveguide of 1, wherein said mode converting section converts at least one percent of the low order modes transmitted into its proximal end into high order modes at the distal end of said mode converting section.

9. A system for fluorescent assays, comprising:

(a) a mode converting multimode sensing waveguide having:

(1) a distal end section including a mode converting section having a proximal end and a distal end and a V number which is higher at said proximal end than at said distal end, said V number changing from said proximal end to said distal end at a rate sufficiently gradual that essentially no transmission loss occurs through said mode converting section, the difference in V numbers between said proximal end and said distal end being sufficient to convert a significant number of low order modes of an excitation wave transmitted from said proximal end of said distal end section to high order mode at said distal end of said distal end section, said distal end of said distal end section corresponding to a distal end of said waveguide and being coated with a tagging component for forming a fluorescent binding pair with an analyte; and (2) a proximal end section of essentially constant V number extending from said proximal end of said distal end section to a proximal end of said waveguide; and (b) a light source adjacent to the proximal end of said waveguide for launching excitation light into the proximal end of said waveguide.

10. The system of claim 9, wherein said mode converting section is inwardly tapered from its proximal end and said proximal end of said waveguide has an essentially constant diameter.

11. The system of claim 9, wherein the ratio of the V number at the distal end of said mode converting section to the V number at the proximal end of said mode converting section is greater than about 2.

12. The system of 11, wherein the ratio of the V number at the distal end of said mode converting section to the V number at the proximal end of said mode converting section is greater than about 3.

13. The system of claim 9, wherein said waveguide is a fiber.

14. The system of claim 9, wherein said proximal end section is has a cladding and the portion of said waveguide from the mode converting section to the distal end of said waveguide is unclad.

15. The system of claim 9, wherein said mode converting section has a dopant concentration which gradually changes from the distal end of said mode converting section to the proximal end of said mode converting section so as to gradually increase the refractive index of said waveguide from the distal end of said mode converting section to the proximal end of said mode converting section.

16. The system of 9, wherein the said mode converting section converts at least one percent of the low order modes transmitted into its proximal end into high order modes at the distal end of said mode converting section.

* * * * *